United States Patent [19]

Fancher et al.

[11] 4,233,318
[45] Nov. 11, 1980

[54] BIOCIDAL ISOTHIOUREA COMPOUNDS

[75] Inventors: Llewellyn W. Fancher; Don R. Baker, both of Orinda, Calif.

[73] Assignee: Stauffer Chemical Company, Westport, Conn.

[21] Appl. No.: 22,755

[22] Filed: Mar. 22, 1979

Related U.S. Application Data

[63] Continuation of Ser. No. 815,975, Jul. 15, 1977, abandoned.

[51] Int. Cl.$^3$ .................. C07C 123/00; C07D 213/74; A01N 43/40; A01N 47/42
[52] U.S. Cl. ................................. 424/326; 424/263; 424/285; 260/347.2; 260/453.4; 546/305
[58] Field of Search ..................... 260/347.2, 564 E; 546/305; 71/94; 424/263, 285, 326

[56] References Cited

U.S. PATENT DOCUMENTS

| | | | |
|---|---|---|---|
| 3,371,010 | 2/1968 | Hamilton et al. | 424/322 |
| 3,513,197 | 5/1970 | Daum et al. | 260/564 E |

OTHER PUBLICATIONS

Hino et al., Chemical and Pharmaceutical Bulletin, vol. 14, No. 11, Nov. 1966 (Japan).

Westland et al., Journal of Medicinal Chemistry, vol. 11, No. 1, Jan. 1968.

*Primary Examiner*—Alan L. Rotman
*Attorney, Agent, or Firm*—Michael J. Bradley

[57] ABSTRACT

Novel biocidal S-aminoalkyl isothiourea compounds have the general structural formula

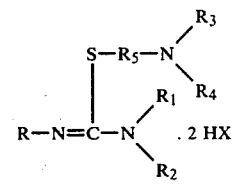

wherein X is halogen; R is a straight or branched chain alkyl radical containing 5 to 20 carbon atoms; $R_1$ is selected from the group consisting of alkyl containing 1 to 20 carbon atoms, alkenyl containing 2 to 6 carbon atoms, benzyl, halo substituted benzyl, α-methyl benzyl, furfuryl and pyridyl methyl; $R_2$ is hydrogen or alkyl containing 1 to 10 carbon atoms; $R_3$ and $R_4$ are independently hydrogen or alkyl containing 1 to 4 carbon atoms; and $R_5$ is divalent alkylene containing 2 to 4 carbon atoms.

60 Claims, No Drawings

BIOCIDAL ISOTHIOUREA COMPOUNDS

This is a continuation, of application Ser. No. 815,975, filed July 15, 1977, now abandoned.

This invention relates to novel biocidal isothiourea compounds.

The novel compounds of this invention have the general structural formula

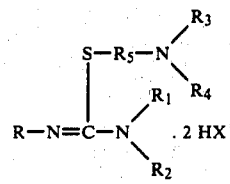

wherein X is halogen, R is a straight or branched chain alkyl radical containing 5 to 20 carbon atoms, $R_1$ is selected from the group consisting of alkyl containing 1 to 20 carbon atoms, alkenyl containing 2 to 6 carbon atoms, benzyl, halo substituted benzyl, α-methyl benzyl, furfuryl and pyridyl methyl; $R_2$ is hydrogen or alkyl containing 1 to 10 carbon atoms; $R_3$ and $R_4$ are independently hydrogen or alkyl containing 1 to 4 carbon atoms; and $R_5$ is divalent alkylene containing 2 to 4 carbon atoms are effective biocidal agents effective against bacteria and fungi. Another embodiment of this invention comprises a method of controlling bacteria or fungi by applying to the locus where such control is desired an effective amount of the novel biocidal compounds described above.

As stated above, the novel biocidal compounds of this invention have the general structural formula

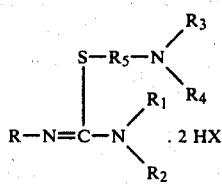

In this formula:

X represents halogen, preferably bromine or chlorine.

R represents an alkyl radical containing 5 to 20 carbon atoms. Illustrative alkyl radicals include pentyl, hexyl, heptyl, octyl, nonyl, decyl, undecyl, dodecyl, and the like. Particularly preferred are straight chain alkyl radicals containing 7 to 16 carbon atoms.

$R_1$ represents a radical selected from the group consisting of alkyl containing 1 to 20 carbon atoms, alkenyl containing 2 to 6 carbon atoms, benzyl, halo substituted benzyl, -methyl benzyl, furfuryl and pyridyl methyl. In this definition the term alkyl includes straight and branched chain alkyl radicals containing 1 to 20 carbon atoms, for example, methyl, ethyl, propyl, butyl, pentyl, hexyl, heptyl, 1-methylheptyl, octyl, nonyl, dodecyl, and the like. Alkyl radicals containing 5 to 12 carbon atoms are preferred. The term alkenyl includes straight and branched chain alkenyl radicals containing 2 to 6 carbon atoms, for example ethenyl, propenyl, butenyl and the like. Alkenyl radicals containing 2 to 4 carbon atoms are preferred.

$R_2$ represents hydrogen or a straight or branched chain alkyl radical containing 1 to 10 carbon atoms, for example, methyl, ethyl, pentyl, hexyl, heptyl, octyl, decyl and the like. Straight chain alkyl radicals containing 5 to 7 carbon atoms are preferred.

$R_3$ and $R_4$ are independently hydrogen or alkyl containing 1 to 4 carbon atoms, for example, methyl, ethyl, propyl, isopropyl, butyl, isobutyl, sec-butyl or tert-butyl.

$R_5$ represents a divalent alkylene radical containing 2 to 4 carbon atoms, preferably

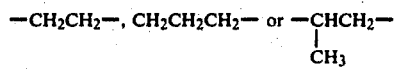

The term biocidal is used in this specification and claims to mean a compound which exhibits fungicidal or bactericidal activity. The term fungicide is used to mean a compound which prevents, destroys or inhibits the growth of fungi. The more active compounds of this invention have particular utility as foliar fungicides protecting tomato plants from tomate early blight and Kentucky bluegrass from bluegrass leaf spot. Many of the compounds are active bactericides, that is, they prevent, destroy or inhibit the growth of bacteria.

The compounds of this invention can be prepared by the generalized reaction shown below:

Step 1:

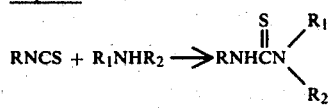

Step 2:

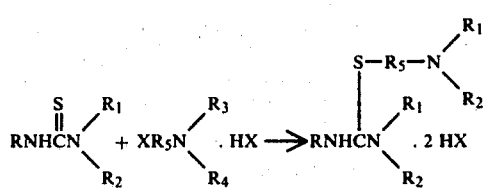

wherein X, $R_1$, $R_2$, $R_3$, $R_4$, and $R_5$ are as defined above.

In Step 1, an isothiocyanate is reacted with ammonia or a primary or secondary amine to give the corresponding thiourea. In this reaction, any inert solvent in which the reactants are soluble, such as hydrocarbons and alcohols, can be used. The reaction is usually moderately exothermic and can be brought to completion by refluxing the reaction mixture. The thiourea thus produced can be recovered by conventional methods, such as evaporation of the solvent under vacuum.

In step 2, the thiourea prepared in Step 1 is reacted with a haloalkylamine hydrohalide. Any inert solvent in which the hydrohalide is soluble can be used. For ease of isolation of the product ethanol is the preferred solvent. The reaction is accomplished by refluxing for several hours with a minimum of about six hours to obtain maximum yields. The product is recovered by conventional techniques, for example, by evaporation of the solvent under vacuum. Further purification can be effected if desired by treatment with other solvents, such as acetone, benzene, ether and the like.

The following examples illustrate the preparation of typical compounds of this invention.

EXAMPLE 1

This example illustrates the preparation of 1-n-heptyl-3-n-octyl-S-β-aminoethylisothiourea dihydrobromide.

To a solution of 3.14 grams (0.02 mole) n-heptylisothiocyanate dissolved in 15 milliliters of benzene is added 2.58 grams (0.02 mole) n-octylamine. The temperature rose to 41° C. The mixture was then refluxed on a steam-bath for about 20 minutes, until the mixture reached a neutral pH. The solution was then evaporated under vacuum. A yield of 6.03 grams of 1-n-heptyl-3-n-octylthiourea was obtained.

To this product were added 4.10 grams (0.02 mole) bromoethylamine hydrobromide and 25 milliliters of ethanol 2B. The mixture was refluxed on a steam-bath for about one hour and permitted to stand overnight. The mixture was refluxed for an additional six hours. The mixture was then evaporated over vacuum. The resulting solid was slurried in acetone, cooled in an ice bath, filtered and washed three times with 5 milliliters of acetone then three times with 5 milliliters of hexane and dried at ambient temperature. A yield of 8.36 grams of a white solid, melting point = 168°-173° C., was obtained. The structure of the product was confirmed by NMR.

EXAMPLE 2

This example illustrates the preparation of 1-n-heptyl-S-β-aminoethyl isothiourea dihydrobromide.

A mixture of 5.77 grams (0.03 mole) of n-heptyl thiourea, 6.7 grams (0.03 mole) of bromoethylamine hydrobromide, and 35 milliliters of ethanol 2B was refluxed on a steam bath for six hours. The mixture was evaporated under vacuum. The resulting viscous, glass-like liquid was slurried in 25 milliliters of hot acetone, cooled on an ice bath, and the acetone was decanted. This procedure was repeated and the residual acetone removed by evaporation under vacuum. A yield of 11.5 grams of a viscous glass-like liquid, $N_D^{30}$-1.5672, was obtained. The structure of the product was confirmed by NMR.

EXAMPLE 3

This example illustrates the preparation of 1-n-heptyl-3-diethyl-S-β-aminoethylisothiourea dihydrobromide.

To a solution of 3.14 grams (0.02 mole) of heptyl isothiocyanate dissolved in 15 milliliters of benzene was added 1.46 grams (0.02 mole) of diethylamine. The temperature rose to about 50° C. The mixture was refluxed on a steam bath for 20 minutes until a neutral pH was obtained. The mixture was then evaporated under vacuum to give 4.8 grams of n-heptyl-diethyl-thiourea. To this product, 4.1 grams (0.02 mole) of bromoethylamine hydrobromide and 25 milliliters of ethanol 2B was added. The mixture was refluxed on a steam bath for four hours and then permitted to stand overnight at ambient temperature. The mixture was then refluxed an additional three hours. The mixture was evaporated under vacuum to yield 8.83 grams of a yellow gel-like liquid, $N_D^{30} = 1.5410$. The structure of the product was confirmed by NMR.

EXAMPLE 4

This example illustrates the preparation of 1,3-di-n-heptyl-S-β-diethylaminoethyl isothiourea dihydrochloride A mixture of 5.44 grams (0.02 mole) of di-n-heptylthiourea, 3.44 grams (0.02 mole) of diethylaminoethyl chloride.hydrochloride and 25 milliliters of ethanol 2B was refluxed on a steam bath for 14 hours. The mixture was then evaporated under vacuum to yield 9.4 grams of a viscous cloudy liquid, $N_D^{30} = 1.5034$. The structure of the product was confirmed by NMR.

EXAMPLE 5

This example illustrates the preparation of 1-n-heptyl-3-allyl-S-β-aminoethyl isothiourea dihydrobromide.

The procedure of Example 1 was repeated using 3.14 grams of n-heptyl isothioucyanate and 1.14 grams of allyl amine to yield 4.30 grams of 1-n-heptyl-3-allyl thiourea, a white clear liquid, $N_D^{30} = 1.5244$.

The 1-n-heptyl-3-allyl thiourea was reacted with 4.1 grams of bromoethylamine hydrobromide in 25 milliliters of ethanol 2B also as described in Example 1. A yield of 6.15 grams of white solid, melting point 151°-154° C., was obtained. The structure of the product was confirmed by NMR.

EXAMPLE 6

This example illlustrates the preparation of 1-n-heptyl-3-benzyl-S-β-aminoethyl isothiourea dihydrobromide.

To a solution of 3.1 grams (0.02 mole) of n-heptyl isothiocyanate dissolved in 25 milliliters of benzene, was added 2.1 grams (0.02 mole) benzylamine. The resulting exothermic reaction resulted in a temperature rise from 24° C. to 35° C. The mixture was then refluxed for 20 minutes on the steam-bath until the mixture reaced neutral pH and the mixture was evaporated under vacuum to yield 5.6 grams of n-heptyl-3-benzyl thiourea, $N_D^{30} = 1.5513$.

To this product was added 4.1 grams (0.02 mole) of bromoethylamine hydrobromide and 25 milliliters of ethanol 2B. The mixture was refluxed on the steam bath for seven hours then evaporated under vacuum to yield a solid. The solid was slurried in 25 milliliters of hot acetone and cooled on an ice bath. The mixture was filtered and the solid washed 4 times with 5 milliliters of acetone and 3 times with 5 milliliters of hexane. The solid was dried at 50° C. to yield 6.6 grams (65% of theory) of a solid, melting point = 193°-195° C. Structure of the product was confirmed by NMR.

EXAMPLE 7

This example illustrates the preparation of 1-ethyl-3-benzyl-S-β-diethylaminoethyl isothiourea dihydrochloride.

To a mixture of 1.74 grams (0.02 mole) of ethyl isothiocyanate and 25 milliliters of benzene was added 2.14 grams (0.02 mole) of benzylamine. The temperature rose from 25° C. to 41° C. The reaction mixture was then refluxed on a steam bath for about 20 minutes to bring the reaction to completion. The mixture was evaporated under vacuum to give 3.67 grams of 1-ethyl-3-benzyl thiourea.

To the 1-ethyl-3-benzyl thiourea was added 3.44 grams (0.02 mole) of diethylaminoethyl chloride.hydrochloride and 25 milliliters of ethanol 2B. The mixture was refluxed on a steam bath overnight. The mixture was then evaporated under vacuum to yield 7.84 grams of a viscous amber-colored liquid, $N_D^{30} = 1.5425$. The structure of the product was confirmed by NMR.

EXAMPLE 8

This example illustrates the preparation of 1-n-heptyl-3-furfuryl-S-β-aminoethyl isothiourea dihydrobromide.

To a mixture of 3.1 grams (0.02 mole) of n-heptyl isothiocyanate and 25 milliliters of benzene was added 1.77 milliliters (0.02 mole) of furfuryl amine. The mixture was refluxed for 30 minutes on a steam bath and then evaporated under vacuum to yield 1-n-heptyl-3-furfuryl thiourea. The product was cooled and 4.1 grams (0.02 mole) of bromoethylamine hydrobromide and 25 milliliters of ethanol 2B was added. The resulting mixture was refluxed on a steam bath overnight. The solid product was removed by filtration and air dried. A yield of 5.2 grams of solid, melting point 140°–145° C., was obtained. Structure of the product was confirmed by NMR.

EXAMPLE 9

This example illustrates the preparation of 1-n-heptyl-3-(2'-pyridylmethyl)-S-aminoethyl isothiouronium dihydrobromide.

The procedure described in Example 8 was repeated using 3.65 milliliters (0.02 mole) n-heptylisothiocyanate, 25 milliliters of benzene and 2.06 milliliters (0.02 mole) of 2-aminoethylpyridine to form the corresponding thiourea which was then reacted with 4.1 grams (0.02 mole) of bromoethylamine hydrobromide in 25 milliliters of ethanol 2B. The yield of 7.1 grams of a semisolid product was obtained. The structure of the product was confirmed by NMR.

The compounds listed in the following Table I include the compounds prepared above and are illustrative of the compounds encompassed by the present invention. These compounds can be prepared in an analogous manner to those whose preparation is described in detail above. Appropriate starting materials will be readily apparent to one skilled in the art.

TABLE I $$RN=C-N\begin{array}{c}S-R_5-N\begin{array}{c}R_3\\ R_4\end{array}\\ R_1\\ R_2\end{array} \cdot 2HX$$

| Compound No. | R | $R_1$ | $R_2$ | $R_3$ | $R_4$ | $R_5$ | X | Physical Constant |
|---|---|---|---|---|---|---|---|---|
| 1 | n-$C_7H_{15}$— | -n-$C_7H_{15}$ | H | H | H | —$CH_2CH_2$— | Br | m.p. 175°–177° C. |
| 2 | n-$C_7H_{15}$— | -n-$C_6H_{13}$ | H | H | H | —$CH_2CH_2$— | Br | m.p. 173°–177° C. |
| 3 | n-$C_7H_{15}$— | -n-$C_5H_{11}$ | H | H | H | —$CH_2CH_2$— | Br | m.p. 156°–159° C. |
| 4 | n-$C_7H_{15}$— | -n-$C_4H_9$ | H | H | H | —$CH_2CH_2$— | Br | m.p. 150°–143° C. |
| 5 | n-$C_7H_{15}$— | -n-$C_3H_7$ | H | H | H | —$CH_2CH_2$— | Br | m.p. 130°–133° C. |
| 6 | n-$C_7H_{15}$— | —$C_2H_5$ | H | H | H | —$CH_2CH_2$— | Br | m.p. 123°–125° C. |
| 7 | n-$C_7H_{15}$— | —$CH_3$ | H | H | H | —$CH_2CH_2$— | Br | m.p. 151°–154° C. |
| 8 | n-$C_7H_{15}$— | —CH(CH$_2$)$_4$CH$_3$<br>$\mid$<br>CH$_3$ | H | H | H | —$CH_2CH_2$— | Br | $n_D^{30}$ 1.5190 |
| 9 | n-$C_7H_{15}$— | -n-$C_8H_{17}$ | H | H | H | —$CH_2CH_2$— | Br | m.p. 168°–173° C. |
| 10 | n-$C_7H_{15}$— | -n-$C_9H_{19}$ | H | H | H | —$CH_2CH_2$— | Br | m.p. 70.5°–72.5° C. |
| 11 | n-$C_7H_{15}$— | -n-$C_{10}H_{21}$ | H | H | H | —$CH_2CH_2$— | Br | m.p. 169°–171° C. |
| 12 | n-$C_7H_{15}$— | -n-$C_{12}H_{25}$ | H | H | H | —$CH_2CH_2$— | Br | m.p. 172°–174° C. |
| 13 | n-$C_7H_{15}$— | -n-$C_{16}H_{33}$ | H | H | H | —$CH_2CH_2$— | Br | m.p. 171°–175° C. |
| 14 | n-$C_6H_{13}$— | -n-$C_6H_{13}$ | H | H | H | —$CH_2CH_2$— | Br | m.p. 174°–176° C. |
| 15 | n-$C_8H_{17}$— | -n-$C_8H_{17}$ | H | H | H | —$CH_2CH_2$— | Br | m.p. 177°–178° C. |
| 16 | n-$C_7H_{15}$— | —$CH_2CH=CH_2$ | H | H | H | —$CH_2CH_2$— | Br | m.p. 151°–154° C. |
| 17 | n-$C_7H_{15}$— | H | H | H | H | —$CH_2CH_2$— | Br | $n_D^{30}$ 1.5672 |
| 18 | n-$C_{10}H_{21}$— | H | H | H | H | —$CH_2CH_2$— | Br | $n_D^{30}$ 1.5610 |
| 19 | n-$C_{12}H_{25}$— | H | H | H | H | —$CH_2CH_2$— | Br | waxy solid |
| 20 | n-$C_7H_{15}$— | —$CH_3$ | —$CH_3$ | H | H | —$CH_2CH_2$— | Br | $n_D^{30}$ 1.5410 |
| 21 | n-$C_7H_{15}$— | -n-$C_3H_7$ | -n-$C_3H_7$ | H | H | —$CH_2CH_2$— | Br | $n_D^{30}$ 1.5277 |
| 22 | n-$C_7H_{15}$— | -n-$C_5H_{11}$ | -n-$C_5H_{11}$ | H | H | —$CH_2CH_2$— | Br | $n_D^{30}$ 1.5244 |
| 23 | n-$C_7H_{15}$— | H | -n-$C_7H_{15}$ | $C_2H_5$ | $C_2H_5$ | —$CH_2CH_2$— | Cl | $n_D^{30}$ 1.5034 |
| 24 | n-$C_7H_{15}$— | H | H | $C_2H_5$ | $C_2H_5$ | —$CH_2CH_2$— | Cl | $n_D^{30}$ ~1.5200 |
| 25 | n-$C_{10}H_{21}$— | H | H | $C_2H_5$ | $C_2H_5$ | —$CH_2CH_2$— | Cl | $n_D^{30}$ 1.5105 |
| 26 | n-$C_{12}H_{25}$— | H | H | $C_2H_5$ | $C_2H_5$ | —$CH_2CH_2$— | Cl | $n_D^{30}$ 1.5033 |
| 27 | n-$C_7H_{15}$— | H | H | $CH_3$ | $CH_3$ | —$CH_2CH_2$— | Br | $n_D^{30}$ ~1.5520 |
| 28 | n-$C_7H_{15}$— | H | H | $CH_3$ | $CH_3$ | —CHCH$_2$—<br>$\mid$<br>CH$_3$ | Br | $n_D^{30}$ 1.5100 |
| 29 | n-$C_7H_{15}$— | H | H | $CH_3$ | $CH_3$ | —$CH_2CH_2CH_2$— | Cl | $n_D^{30}$ 1.5160 |
| 30 | n-$C_7H_{15}$— | H | H | H | H | —$CH_2CH_2CH_2$— | Br | $n_D^{30}$ 1.5670 |
| 31 | n-$C_7H_{15}$ | H | n-$C_7H_{15}$ | $CH_3$ | $CH_3$ | —$CH_2CH_2$— | Br | $n_D^{30}$ 1.5133 |
| 32 | n-$C_7H_{15}$— | H | n-$C_7H_{15}$ | H | H | —$CH_2CH_2CH_2$— | Br | $n_D^{30}$ 1.5200 |
| 33 | n-$C_7H_{15}$— | H | n-$C_7H_{15}$ | $CH_3$ | $CH_3$ | —CHCH$_2$—<br>$\mid$<br>CH$_3$ | Cl | waxy solid |
| 34 | n-$C_7H_{15}$— | H | n-$C_7H_{15}$ | $CH_3$ | $CH_3$ | —$CH_2CH_2CH_2$— | Cl | waxy solid |
| 35 | n-$C_5H_{11}$— | —CH$_2$—⟨phenyl⟩ | H | H | H | —$CH_2CH_2$— | Br | m.p. 112°–115° C. |
| 36 | n-$C_7H_{15}$— | —CH$_2$—⟨phenyl⟩ | H | H | H | —$CH_2CH_2$— | Br | m.p. 193°–195° C. |

TABLE I-continued

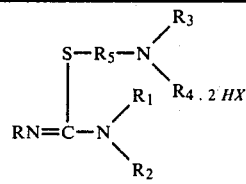

| Compound No. | R | R₁ | R₂ | R₃ | R₄ | R₅ | X | Physical Constant |
|---|---|---|---|---|---|---|---|---|
| 37 | n-C₈H₁₇— | —CH₂—⟨phenyl⟩ | H | H | H | —CH₂CH₂— | Br | m.p. 189°–192° C. |
| 38 | n-C₁₀H₂₁— | —CH₂—⟨phenyl⟩ | H | H | H | —CH₂CH₂— | Br | m.p. 194°–196° C. |
| 39 | n-C₆H₁₃— | —CH₂—⟨phenyl⟩ | H | H | H | —CH₂CH₂— | Br | m.p. 196°–199° C. |
| 40 | n-C₉H₁₉— | —CH₂—⟨phenyl⟩ | H | H | H | —CH₂CH₂— | Br | m.p. 194°–196° C. |
| 41 | n-C₇H₁₅— | —CH₂—⟨2,4-dichlorophenyl⟩ | H | H | H | —CH₂CH₂— | Br | m.p. 210° C. |
| 42 | n-C₇H₁₅— | —CH(CH₃)—⟨phenyl⟩ | H | H | H | —CH₂CH₂— | Br | plastic |
| 43 | n-C₇H₁₅— | —CH₂—⟨furyl⟩ | H | H | H | —CH₂CH₂— | Br | m.p. 140°–145° C. |
| 44 | n-C₇H₁₅— | —CH₂—⟨pyridyl⟩ | H | H | H | —CH₂CH₂— | Br | semi-solid |

As stated above, the compounds of this invention are active fungicides and bactericides. The following fungicidal tests were conducted and the results are reported in Table II.

IN VITRO TESTS

In-Vitro Fungicide Bioassay

Test chemicals are diluted in acetone to a concentration of 2500 ppm. Test cultures are prepared by adding 0.1 milliliter of cultures of either *Aspergillus niger* or *Penicillium italicum* to 16×100 mm test tubes containing 5 milliliters of sterile malt extract broth. One-tenth milliliter of the stock chemical solution is then added to each test tube for a final concentration of 50 ppm, and the tubes are maintained at 27° C. for one week. Each tube is then examined for the presence or absence of a mycelial mat. Chemicals which show control at 50 ppm are retested at progressively lower levels until the minimum concentration giving 75% or greater control is determined.

In-Vitro Bactericide Bioassay

Test chemicals are diluted in acetone to a concentration of 2500 ppm. Test cultures are prepared by adding 0.1 milliliter of cultures of *E. Coli, Staph. aureus,* or *Erwinia amylovora* to 16×100 mm test tubes containing 5 milliliters of sterile nutrient broth. One-tenth milliliter of the stock chemical solution is then added to each test tube for a final concentration of 50 ppm and the tubes are maintained at 27° C. for one week. Each tube is then examined for the presence or absence of turbidity due to the growth of the bacterium. Chemicals which show control at 50 ppm are retested at progressively lower levels until the minimum concentration giving 75% or greater control is determined.

FOLIAR FUNGICIDE TESTS

Bean Rust

Test chemicals are dissolved in an appropriate solvent and then further diluted with a 50:50 acetone-water solution. Pinto bean plants (*Phaseolus vulgaris* L.), approximately 15 centimeters tall, are inverted and dipped into the solution for 2–3 seconds. Test concentrations range from 1000 ppm downward. After the leaves have dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as percent reduction in number of pustules as compared to untreated inoculated plants.

Bean Powdery Mildew

Test chemicals are dissolved in an appropriate solvent and then further diluted with a 50:50 acetone-water solution. Pinto bean plants (*Phaseolus vulgaris* L.), approximately 15 centimeters tall, are inverted and dipped into the solution for 2–3 seconds. Test concentrations range from 1000 ppm downward. After the leaves have dried, they are dusted with spores of the powdery mildew fungus (*Erysiphe polygoni* De Candolle) and the plants are retained in the greenhouse until the fungal growth appears in the leaf surface. Effectiveness is recorded as percent of the leaf surface free of fungal growth as compared to untreated inoculated plants.

Tomato Early Blight

Test chemicals are dissolved in an appropriate solvent and then further diluted with a 50:50 acetone-water solution. Tomato plants (*Lycopersicon esculentum*), approximately 4 weeks old, are sprayed to the point of runoff with the test solutions. Test concentrations range from 1000 ppm downward. After the leaves have dried, they are inoculated with a water suspension of spores of the early blight fungus ((*Alternaria solani* Ellis and Martin) and placed in an environment of 100% humidity for 48 hours. The plants are then removed from the humidity chamber and held until disease lesions appear on the leaves. Effectiveness is recorded as percent reduction in number of lesions as compared to untreated inoculated plants.

Bluegrass Leaf Spot

Test chemicals are dissolved in an appropriate solvent and then further diluted with a 50:50 acetone-water solution. "Marion" Kentucky Bluegrass plants (*Poa pratensis* L.), approximately 4 weeks old, are sprayed to the point of runoff with the test solutions. Test concentrations range from 1000 ppm downwards. After the leaves have dried, they are inoculated with a water suspension of *Helminthosporium sativus* Pammel and held a 100% RH for 48 hours. The plants are then held in a greenhouse at 27° C. until disease lesions appear on the leaves. Effectiveness is recorded as percent reduction in number of lesions as compared to untreated inoculated plants.

TABLE II

| Compound No. | In-Vitro | | | | | Foliar Preventative | | | |
|---|---|---|---|---|---|---|---|---|---|
| | Aspergillus niger | Penicillium italicum | E. Coli | Staph. aureus | Erwinia amylovora | Bean Rust | Tomato Powdery Mildew | Tomato Early Blight | Blue Grass Leafspot |
| 1 | >50 | 50 | 50 | 5 | (10) | 500 | 1000 | 500 | 100 |
| 2 | >50 | >50 | >50 | 10 | (5) | 500 | >1000 | 100 | 100 |
| 3 | >50 | >50 | >50 | 10 | 10 | 100 | >1000 | 500 | 500 |
| 4 | >50 | >50 | 25 | 5 | 1 | 500 | >1000 | 500 | 100 |
| 5 | >50 | >50 | >50 | 5 | 25 | 500 | 1000 | 500 | 100 |
| 6 | >50 | >50 | >50 | 25 | 25 | 500 | >1000 | 1000 | 100 |
| 7 | >50 | >50 | >50 | 10 | 5 | 100 | 1000 | >1000 | 100 |
| 8 | >50 | >50 | (25) | 5 | (5) | 500 | >1000 | 500 | 1000 |
| 9 | >50 | 50 | >50 | 25 | 25 | 500 | >1000 | 500 | 500 |
| 10 | >50 | 10 | >50 | 5 | >50 | 500 | >1000 | 100 | 500 |
| 11 | >50 | 1 | >50 | 5 | >50 | 500 | >1000 | 100 | 500 |
| 12 | >50 | 25 | >50 | >50 | >50 | 500 | >1000 | 500 | 500 |
| 13 | >50 | >50 | >50 | >50 | >50 | 1000 | >1000 | 500 | 1000 |
| 14 | >50 | >50 | 10 | 5 | 5 | 500 | >1000 | 100 | 100 |
| 15 | >50 | .063 | >50 | >50 | >50 | 1000 | >1000 | 500 | 100 |
| 16 | >50 | >50 | >50 | 5 | 5 | 1000 | 1000 | 500 | 100 |
| 17 | >50 | >50 | >50 | 10 | (5) | 500 | >1000 | 100 | 100 |
| 18 | >50 | >50 | (50) | 5 | 25 | 1000 | 1000 | 500 | 500 |
| 19 | >50 | >50 | >50 | 25 | >50 | 1000 | 1000 | 1000 | >1000 |
| 20 | >50 | >50 | >50 | 10 | 25 | 1000 | >1000 | 500 | 500 |
| 21 | >50 | >50 | >50 | 10 | (10) | 500 | >1000 | 500 | 500 |
| 22 | >50 | 25 | >50 | 5 | 25 | 500 | >1000 | 500 | 500 |
| 23 | >50 | >50 | >50 | 5 | (5) | 500 | >1000 | — | — |
| 24 | >50 | >50 | >50 | >50 | >50 | 1000 | >1000 | >1000 | >1000 |
| 25 | | | | | | | | | |
| 26 | | | | | | | | | |
| 27 | >50 | >50 | >50 | >50 | >50 | >1000 | >1000 | 1000 | 1000 |
| 28 | >50 | >50 | >50 | >50 | >50 | >1000 | >1000 | 500 | >1000 |
| 29 | >50 | >50 | >50 | >50 | >50 | >1000 | >1000 | 500 | 500 |
| 30 | >50 | >50 | >50 | 10 | 25 | 500 | >1000 | 500 | 100 |
| 31 | >50 | >50 | >50 | 10 | 10 | 1000 | >1000 | 500 | 500 |
| 32 | >50 | >50 | >50 | 10 | 10 | >1000 | >1000 | 500 | 100 |
| 33 | >50 | >50 | >50 | 5 | 50 | 500 | >1000 | 500 | 100 |
| 34 | >50 | >50 | >50 | 5 | 25 | 500 | >1000 | 100 | 500 |
| 35 | >50 | >50 | >50 | 10 | 10 | >1000 | >1000 | >1000 | >1000 |
| 36 | >50 | >50 | 10 | 5 | 5 | >1000 | 1000 | | |
| 37 | >50 | >50 | 25 | 5 | 25 | >1000 | >1000 | 500 | 500 |
| 38 | >50 | >50 | >50 | >50 | 50 | 1000 | >1000 | 1000 | 500 |
| 39 | >50 | >50 | >50 | 5 | 10 | >1000 | >1000 | 1000 | 1000 |
| 40 | >50 | >50 | >50 | 5 | 25 | 1000 | >1000 | | |
| 41 | >50 | >50 | >50 | 5 | 10 | >1000 | >1000 | 500 | 500 |
| 42 | >50 | >50 | >50 | 5 | 10 | 1000 | 1000 | 500 | 100 |
| 43 | >50 | >50 | >50 | 5 | 5 | >1000 | >1000 | 1000 | 500 |
| 44 | >50 | >50 | >50 | 25 | 50 | 1000 | >1000 | >1000 | 500 |

In the above Table II:
>indicates that the compound did not control the growth of that species of bacteriaor fungi at the given concentration of the test compound.
( )indicates that partial control of that species of bacteria or fungi was achievedat the given concentration of the test compound.
—indicates that the compound was not tested with that species of bacteria or fungi The novel compounds of this invention are generally applie to the locus where control of bacteria or fungi is desired in the form of formulations containing the compound and an inert carrier. Such formulations generally take the form of dusts, wettable powders, solutions, emulsifiable concentrates or the like.

Dusts are free-flowing powder compositions containing the active compound impregnated on a particulate carrier. The particle size of the carrier is usually in the range of from about 30 to 50 microns. Examples of suitable carriers are talc, bentonite, diatomaceous earth, and pryrophyllite. Anticaking and antistatic agents can be added, if desired. The composition generally contains up to 50% of active ingredient.

Wettable powders are finely divided compositions comprising a particulate carrier impregnated with the active compound and additionally containing one or more surface active agents. The surface active agents promote rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in *Pesticide Formulations* by Wade Van Valkenburg, Marcel Dekker, Inc., N.W., 1973 at pages 79–84.

Granules comprise the active compound impregnated on a particulate inert carrier having a particle size of 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The active componds can also be applied in the form of a solution in a suitable solvent. Solvents frequently used in pesticidal formulations include kerosene, fuel oil, xylene, petroleum fractions with boiling ranges above xylene, and aromatic petroleum fractions rich in methylated naphthalenes.

Emulsifiable concentrates consist of an oil solution of the active compound along with an emulsifying agent. Prior to use the concentrate is diluted with water to form a suspended emulsion of oil droplets. The emulsifiers used are usually a mixture of anionic and nonionic surfactants. Other additives such as spreadi agents and stickers can be included in the emulsifiable concentrate if desired.

What is claimed is:

1. A compound having the general structural formula

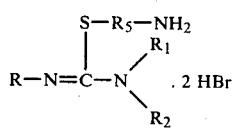

wherein R is a straight or branched chain alkyl radical containing 5 to 20 carbon atoms; $R_1$ is selected from the group consisting of alkyl containing 1 to 20 carbon atoms and alkenyl containing 2 to 6 carbon atoms; $R_2$ is hydrogen or alkyl containing 1 to 10 carbon atoms; and $R_5$ is divalent alkylene containing 2 to 6 carbon atoms.

2. The compound of claim 1 wherein X is Br, R is n—$C_7H_{15}$—, $R_1$ is —n—$C_7H_{15}$—, $R_2$ is H, $R_3$ is H, $R_4$ is H, and $R_5$ is —$CH_2CH_2$—.

3. The compound of claim 1 wherein X is Br, R is —$C_7H_{15}$—, $R_1$ is —n—$C_6H_{13}$, $R_2$ is H, $R_3$ is H, $R_4$ is H, and $R_5$ is —$CH_2CH_2$—.

4. The compound of claim 1 wherein X is Br, R is n—$C_7H_{15}$—, $R_1$ is —n—$C_5H_{11}$, $R_2$ is H, $R_3$ is H, $R_4$ is H, and $R_5$ is —$CH_2CH_2$—.

5. The compound of claim 1 wherein X is Br, R is n—$C_7H_{15}$—, $R_1$ is —n—$C_4H_9$, $R_2$ is H, $R_3$ is H, $R_4$ is H, and $R_5$ is —$CH_2CH_2$—.

6. The compound of claim 1 wherein X is Br, R is n—$C_7H_{15}$—, $R_1$ is —n—$C_3H_7$, $R_2$ is H, $R_3$ is H, $R_4$ is H, and $R_5$ is —$CH_2CH_2$—.

7. The compound of claim 1 wherein X is Br, R is n—$C_7H_{15}$—, $R_1$ is —$C_2H_5$, $R_2$ is H, $R_3$ is H, $R_4$ is H, and $R_5$ is —$CH_2CH_2$—.

8. The compound of claim 1 wherein X is Br, R is n—$C_7H_{15}$—, $R_1$ is —$CH_3$, $R_2$ is H, $R_3$ is H, $R_4$ is H, and $R_5$ is —$CH_2CH_2$—.

9. The compound of claim 1 wherein X is Br, R is n—$C_7H_{15}$—,

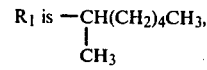

$R_2$ is H, $R_3$ is H, $R_4$ is H, and $R_5$ is —$CH_2CH_2$—.

10. The compound of claim 1 wherein X is Br, R is n—$C_7H_{15}$—, $R_1$ is —n—$C_8H_{17}$, $R_2$ is H, $R_3$ is H, $R_4$ is H, and $R_5$ is —$CH_2CH_2$—.

11. The compound of claim 1 wherein X is Br, R is n—$C_7H_{15}$—, $R_1$ is —n—$C_9H_{19}$, $R_2$ is H, $R_3$ is H, $R_4$ is H, and $R_5$ is —$CH_2CH_2$—.

12. The compound of claim 1 wherein X is Br, R is n—$C_7H_{15}$—, $R_1$ is —n—$C_{10}H_{21}$, $R_2$ is H, $R_3$ is H, $R_4$ is H, and $R_5$ is —$CH_2CH_2$—.

13. The compound of claim 1 wherein X is Br, R is n—$C_7H_{15}$—, $R_1$ is —n—$C_{12}H_{25}$, $R_2$ is H, $R_3$ is H, $R_4$ is H, and $R_5$ is —$CH_2CH_2$—.

14. The compound of claim 1 wherein X is Br, R is n—$C_7H_{15}$—, $R_1$ is —n—$C_{16}H_{33}$, $R_2$ is H, $R_3$ is H, $R_4$ is H, and $R_5$ is —$CH_2CH_2$—.

15. The compound of claim 1 wherein X is Br, R is n—$C_6H_{13}$—, $R_1$ is —n—$C_6H_{13}$, $R_2$ is H, $R_3$ is H, $R_4$ is H, and $R_5$ is —$CH_2CH_2$—.

16. The compound of claim 1 wherein X is Br, R is n—$C_8H_{17}$—, $R_1$ is —n—$C_8H_{17}$—, $R_2$ is H, $R_3$ is H, $R_4$ is H, and $R_5$ is —$CH_2CH_2$—.

17. The compound of claim 1 wherein X is Br, R is n—$C_7H_{15}$—, $R_1$ is —$CH_2CH=CH_2$, $R_2$ is H, $R_3$ is H, $R_4$ is H, and $R_5$ is —$CH_2CH_2$—.

18. The compound of claim 2 wherein X is Br, R is n—$C_7H_{15}$—, $R_1$ is —$CH_3$, $R_2$ is —$CH_3$, $R_3$ is H, $R_4$ is H, and $R_5$ is —$CH_2CH_2$—.

19. The compound of claim 1 wherein X is Br, R is n—$C_7H_{15}$—, $R_1$ is —n—$C_3H_7$, $R_2$ is —n—$C_3H_7$, $R_3$ is H, $R_4$ is H, and $R_5$ is —$CH_2CH_2$—.

20. The compound of claim 1 wherein X is Br, R is n—$C_7H_{15}$—, $R_1$ is —n—$C_5H_{11}$, $R_2$ is —n—$C_5H_{11}$, $R_3$ is H, $R_4$ is H, and $R_5$ is —$CH_2CH_2$—.

21. A compound having the general structural formula

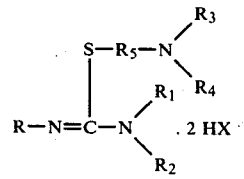

wherein X is halogen; R is a straight or branched chain alkyl radical containing 5 to 20 carbon atoms; $R_1$ is benzyl, halosubstituted benzyl or α-methyl benzyl; $R_2$ is hydrogen or alkyl containing 1 to 10 carbon atoms; $R_3$ and $R_4$ are independently hydrogen or alkyl containing 1 to 4 carbon atoms; and R₅ is divalent alkylene containing 2 to 6 carbon atoms.

22. The compound of claim 21 wherein X is Br, R is n—C₅H₁₁—,

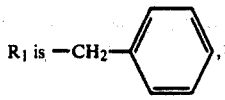

R₂ is H, R₃ is H, R₄ is H, and R₅ is —CH₂CH₂—.

23. The compound of claim 21 wherein X is Br, R is n—C₇H₁₅—,

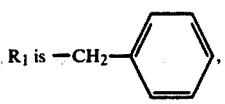

R₂ is H, R₃ is H, R₄ is H, and R₅ is —CH₂CH₂—.

24. The compound of claim 21 wherein X is Br, R is n—C₈H₁₇—,

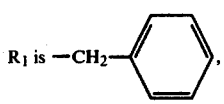

R₂ is H, R₃ is H, R₄ is H, and R₅ is —CH₂CH₂—.

25. The compound of claim 21 wherein X is Br, R is n—C₁₀H₂₁—,

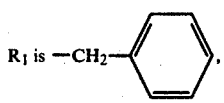

R₂ is H, R₃ is H, R₄ is H, and R₅ is —CH₂CH₂—.

26. The compound of claim 21 wherein X is Br, R is n—C₆H₁₃—,

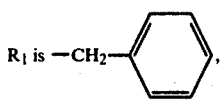

R₂ is H, R₃ is H, R₄ is H, and R₅ is —CH₂CH₂—.

27. The compound of claim 21 wherein X is Br, R is n—C₉H₁₉—,

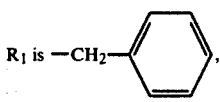

R₂ is H, R₃ is H, R₄ is H, and R₅ is —CH₂CH₂—.

28. The compound of claim 21 wherein X is Br, R is n—C₇H₁₅,

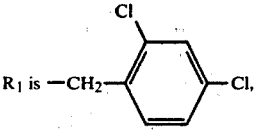

R₂ is H, R₃ is H, R₄ is H, and R₅ is —CH₂CH₂—.

29. The compound of claim 21 wherein X is Br, R is n—C₇H₁₅—,

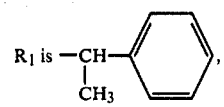

R₂ is H, R₃ is H, R₄ is H, and R₅ is —CH₂CH₂—.

30. A method of controlling a microorganism selected from bacteria and fungi which comprises applying to the locus where such control is desired an effective amount of a compound having the general structural formula

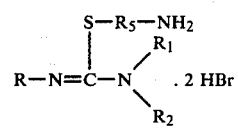

wherein R is a straight or branched chain alkyl radical containing 5 to 20 carbon atoms; R₁ is selected from the group consisting of alkyl containing 1 to 20 carbon atoms and alkenyl containing 2 to 6 carbon atoms; R₂ is hydrogen or alkyl containing 1 to 10 carbon atoms; and R₅ is divalent alkylene containing 2 to 6 carbon atoms.

31. The method of claim 30 wherein X is Br, R is n—C₇H₁₅—, R₁ is —n—C₇H₁₅, R₂ is H, R₃ is H, R₄ is H, and R₅ is —CH₂CH₂—.

32. The method of claim 30 wherein X is Br, R is n—C₇H₁₅—, R₁ is —n—C₆H₁₃, R₂ is H, R₃ is H, R₄ is H, and R₅ is —CH₂CH₂—.

33. The method of claim 30 wherein X is Br, R is n—C₇H₁₅—, R₁ is —n—C₅H₁₁, R₂ is H, R₃ is H, and R₄ is H, and R₅ is —CH₂CH₂—.

34. The method of claim 30 wherein X is Br, R is n—C₇H₁₅—, R₁ is —n—C₄H₉, R₂ is H, R₃ is H, R₄ is H, and R₅ is —CH₂CH₂—.

35. The method of claim 30 wherein X is Br, R is n—C₇H₁₅—, R₁ is —n—C₃H₇, R₂ is H, R₃ is H, R₄ is H, and R₅ is —CH₂CH₂—.

36. The method of claim 30 wherein X is Br, R is n—C₇H₁₅—, R₁ is —C₂H₅, R₂ is H, R₃ is H, R₄ is H, and R₅ is —CH₂CH₂—.

37. The method of claim 30 wherein X is Br, R is n—C₇H₁₅—, R₁ is —CH₃, R₂ is H, R₃ is H, R₄ is H, and R₅ is —CH₂CH₂—.

38. The method of claim 30 wherein X is Br, R is n—C₇H₁₅—,

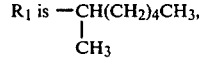

R₂ is H, R₃ is H, R₄ is H, and R₅ is —CH₂CH₂—.

39. The method of claim 30 wherein X is Br, R is n—C₇H₁₅—, R₁ is —n—C₈H₁₇, R₂ is H, R₃ is H, R₄ is H, and R₅ is —CH₂CH₂—.

40. The method of claim 30 wherein X is Br, R is n—C₇H₁₅—, R₁ is —n—C₉H₁₉, R₂ is H, R₃ is H, R₄ is H and R₅ is —CH₂CH₂—.

41. The method of claim 30 wherein X is Br, R is n—C₇H₁₅—, R₁ is —n—C₁₀H₂₁, R₂ is H, R₃ is H, R₄ is H, and R₅ is —CH₂CH₂—.

42. The method of claim 30 wherein X is Br, R is n—C₇H₁₅—, R₁ is —n—C₁₂H₂₅, R₂ is H, R₃ is H, R₄ is H, and R₅ is —CH₂CH₂—.

43. The method of claim 30 wherein X is Br, R is n—C₇H₁₅—, R₁ is —n—C₁₆H₃₃, R₂ is H, R₃ is H, R₄ is H, and R₅ is —CH₂CH₂—.

44. The method of claim 30 wherein X is Br, R is n—C₆H₁₃—, R₁ is —n—C₆H₁₃, R₂ is H, R₃ is H, R₄ is H, and R₅ is —CH₂CH₂—.

45. The method of claim 30 wherein X is Br, R is n—C₈H₁₇— R₁ is —n—C₈H₁₇, R₂ is H, R₃ is H, R₄ is H, and R₅ is —CH₂CH₂—.

46. The method of claim 30 wherein X is Br, R is n—C₇H₁₅— R₁ is —CH₂CH=CH₂, R₂ is H, R₃ is H, R₄ is H, and R₅ is —CH₂CH₂—.

47. The method of claim 30 wherein X is Br, R is n—C₇H₁₅—, R₁ is —CH₃, R₂ is —CH₃, R₃ is H, R₄ is H, and R₅ is —CH₂CH₂—.

48. The method of claim 30 wherein X is Br, R is n—C₇H₁₅—, R₁ is —n—C₃H₇, R₂ is —n—C₃H₇, R₃ is H, R₄ is H, and R₅ is —CH₂CH₂—.

49. The method of claim 30 wherein X is Br, R is n—C₇H₁₅— R₁ is —n—C₅H₁₁, R₂ is —n—C₅H₁₁, R₃ is H, R₄ is H, and R₅ is —CH₂CH₂.

50. A method of claim 30 having the general structural formula

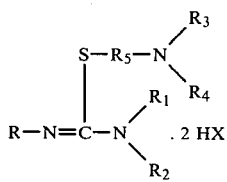

wherein X is halogen; R is a straight or branched chain alkyl radical containing 5 to 20 carbon atoms; R₁ is benzyl, halo-substituted benzyl or α-methyl benzyl; R₂ is hydrogen or alkyl containing 1 to 10 carbon atoms; R₃ and R₄ are independently hydrogen or alkyl containing 1 to 4 carbon atoms; and R₅ is divalent alkylene containing 2 to 6 carbon atoms.

51. The method of claim 50 wherein X is Br, R is n—C₅H₁₁,

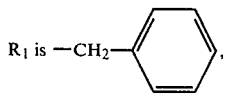

R₂ is H, R₃ is H, R₄ is H, and R₅ is —CH₂CH₂—.

52. The method of claim 50 wherein X is Br, R is n—C₇H₁₅,

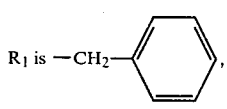

R₂ is H, R₃ is H, R₄ is H, and R₅ is —CH₂CH₂—.

53. The method of claim 50 wherein X is Br, R is n—C₈H₁₇,

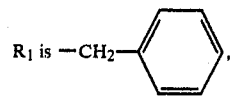

R₂ is H, R₃ is H, R₄ is H, and R₅ is —CH₂CH₂—.

54. The method of claim 50 wherein X is Br, R is n—C₁₀H₂

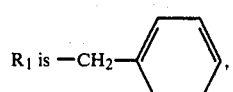

R₂ is H, R₃ is H, R₄ is H, and R₅ is —CH₂CH₂—.

55. The method of claim 50 wherein X is Br, R is n—C₆H₁₃

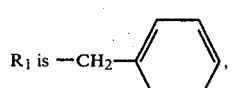

R₂ is H, R₃ is H, R₄ is H, and R₅ is —CH₂CH₂—.

56. The method of claim 50 wherein X is Br, R is n—C₉H₁₉—

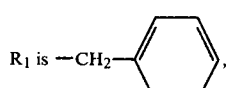

R₂ is H, R₃ is H, R₄ is H, and R₅ is —CH₂CH₂—.

57. The method of claim 50 wherein X is Br, R is n—C₇H₁₅—

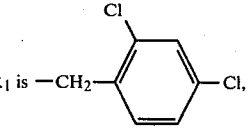

R₂ is H, R₃ is H, R₄ is H, and R₅ is —CH₂CH₂—.

58. The method of claim 50 wherein X is Br, R is n—C₇H₁₅—

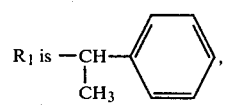

R₂ is H, R₃ is H, R₄ is H, and R₅ is —CH₂CH₂—.

59. An antimicrobial composition comprising a compound having the general structural formula

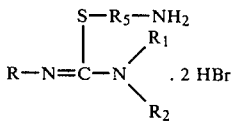

wherein R is a straight or branched chain alkyl radical containing 5 to 20 carbon atoms; R₁ is selected from the group consisting of alkyl containing 1 to 20 carbon atoms and alkenyl containing 2 to 6 carbon atoms; $R_2$ is hydrogen or alkyl containing 1 to 10 carbon atoms; and $R_5$ is divalent alkylene containing 2 to 6 carbon atoms and an inert carrier therefore.

60. An antimicrobial composition comprising a compound having the general structural formula

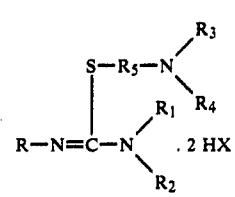

wherein X is halogen; R is a straight or branched chain alkyl radical containing 5 to 20 carbon atoms; $R_1$ is benzyl, halo-substituted benzyl or α-methyl benzyl; $R_2$ is hydrogen or alkyl containing 1 to 10 carbon atoms; $R_3$ and $R_4$ are independently hydrogen or alkyl containing 1 to 4 carbon atoms; and $R_5$ is divalent alkylene containing 2 to 6 carbon atoms and an inert carrier therefore.

* * * * *

UNITED STATES PATENT AND TRADEMARK OFFICE
CERTIFICATE OF CORRECTION

PATENT NO. : 4,233,318
DATED : November 11, 1980
INVENTOR(S) : Llewellyn W. Fancher, et al.

It is certified that error appears in the above—identified patent and that said Letters Patent is hereby corrected as shown below:

Column 2, line 23, please change ...tomate... to read ---tomato---.

Column 2, line 40, please change the formula to read

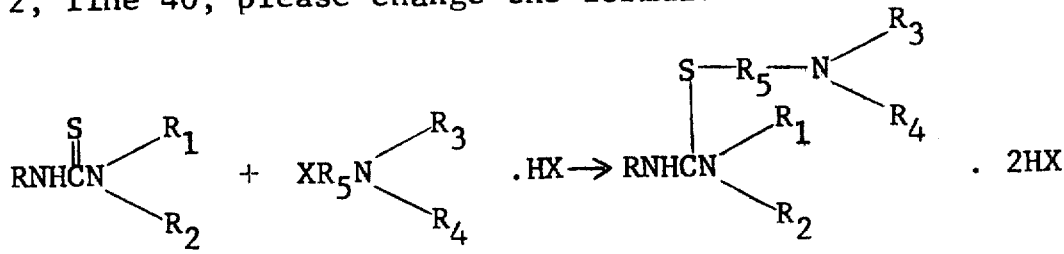

Column 4, line 11, please change ...isothioucyanate... to read ---isothiocyanate---.

Column 4, line 31, please change ...reaced... to read ---reached---.

UNITED STATES PATENT AND TRADEMARK OFFICE
CERTIFICATE OF CORRECTION

PATENT NO. : 4,233,318

DATED : November 11, 1980

INVENTOR(S) : Llewellyn W. Fancher, et al.

It is certified that error appears in the above—identified patent and that said Letters Patent is hereby corrected as shown below:

Column 9, line 58, please change ...((Alternaria... to read ---(Alternaria---.

Column 10, line 59, please change ...applie... to read ---applied---.

Table II, Compound 1, under headings "italicum" and "Coli", please change the "50" to read ">50".

Column 11, line 37, please change ...spreadi... to read ---spreading---.

Column 12, line 43 (Claim 18), please change the ---2--- to ---1---.

Column 16, line 9 (Claim 54), please change ...n-$C_{10}H_2$... to read ---n-$C_{10}H_{21}$---.

Signed and Sealed this

Seventeenth Day of November 1981

[SEAL]

Attest:

GERALD J. MOSSINGHOFF

Attesting Officer     Commissioner of Patents and Trademarks